(12) United States Patent
Makin et al.

(10) Patent No.: US 6,534,065 B1
(45) Date of Patent: Mar. 18, 2003

(54) INFLUENZA VACCINE COMPOSITION WITH CHITOSAN ADJUVANT

(75) Inventors: Jill Catherine Makin, Liverpool (GB); Andrew David Bacon, London (GB)

(73) Assignee: West Pharmaceutical Services Drug Delivery & Clinical Research Centre Limited, Nottingham (GB)

( * ) Notice: Subject to any disclaimer, the term of this patent is extended or adjusted under 35 U.S.C. 154(b) by 0 days.

(21) Appl. No.: 09/583,124

(22) Filed: May 30, 2000

Related U.S. Application Data

(63) Continuation of application No. PCT/GB98/03534, filed on Nov. 27, 1998.

(30) Foreign Application Priority Data

Nov. 28, 1997 (GB) .............................................. 9725084

(51) Int. Cl.$^7$ ............................................ A61K 39/145
(52) U.S. Cl. ............................... 424/206.1; 424/78.08; 424/184.1; 536/20
(58) Field of Search ..................... 424/78.08, 184.1, 424/94.1, 206.1, 278.1, 279.1, 428, 435; 514/23, 54, 55, 888; 536/20; 530/404, 406; 435/7.1

(56) References Cited

U.S. PATENT DOCUMENTS 6,048,536 A    4/2000    Chatfield

FOREIGN PATENT DOCUMENTS

| EP | 0 183 556 A2 | 6/1986 |
|---|---|---|
| EP | 0 460 020 B1 | 4/1994 |
| WO | WO90/09780 A1 | 9/1990 |
| WO | WO96/09805 A2 | 4/1996 |
| WO | WO 96/10421 | 4/1996 |
| WO | WO96/10421 A1 | 4/1996 |
| WO | WO97/16208 A1 | 5/1997 |
| WO | WO 97/20576 | 6/1997 |

OTHER PUBLICATIONS

Nishimura, K., et al., "Immunological activity of chitin and its derivatives", *Vaccine*, 2(1), pp. 93–7, (1984).
Jabal–Gill, Inderjit et al., "Stimulation of mucosal and systemic antibody responses against *Bordetella pertussis* filamentous hemagglutinin and recombinant pertussis toxin after nasal administration with chitosan in mice", *Vaccine* 16(20), pp. 2039–2046, (Dec. 1998).
Edward S. Cahill et al., "Mice are protected against *Bordetella pertussis* infection by intranasal immunization with filamentous haemagglutinin", FEMS Microbiology Letters 107:211–216 (1993).
A de Haan et al., "Mucosal immunoadjuvant activity of liposomes: induction of systemic IgG and secretory IgA responses in mice by intranasal immunization with an influenza subunit vaccine and coadministered liposomes," *Vaccine* 13(2):155–162 (1995).
Patricia L. Hibberd et al., "Immunization Strategies for the Immunocompromised Host: The Need for Immunoadjuvants," *Annals of Internal Medicine* 110(12):955–956 (1989).
Keiko Nishimura et al., "Adjuvant activity of chitin derivatives in mice and guinea–pigs," *Vaccine* 3:379–384 (Dec. 1985).
Tetsuya Oka et al. "Enhancing effects of pertussis toxin B oligomer on the immunogenicity of influenza vaccine administered intranasally," *Vaccine* 12(14):1255–1258 (1994).
A. Bacon et al., "A novel mucosal influenza vaccine," *New Trends in Vaccine R&D*, XP–002098659, p. 98 (1998).

*Primary Examiner*—James Housel
*Assistant Examiner*—Ulrike Winkler
(74) *Attorney, Agent, or Firm*—Akin Gump Strauss Hauer & Feld, L.L.P.

(57) ABSTRACT

A vaccine composition adapted for mucosal administration is provided. The composition includes one or more influenza vaccine antigens and an effective adjuvant amount of an acid addition salt of a chitosan wherein the chitosan is a deacetylated chitin which is at least 80% deacetylated and has a weight average molecular weight of between 10,000 and 100,000.

19 Claims, 3 Drawing Sheets

Fig. 3

HAI RESPONSES TO B/HARBIN (POST SECOND DOSE)

| Sample | |
|---|---|
| PROTASAN GLUTAMATE START MATERIAL | |
| PROTASAN GLUTAMATE FRACTION 2 | |
| PROTASAN GLUTAMATE FRACTION 4 | |
| PROTASAN GLUTAMATE FRACTION 5 | |
| PROTASAN GLUTAMATE FRACTION 5 | |
| PROTASAN GLUTAMATE FRACTION 5 | |
| PROTASAN CHLORIDE START MATERIAL | |
| PROTASAN CHLORIDE FRACTION 1 | |
| PROTASAN CHLORIDE FRACTION 2 | |
| PROTASAN CHLORIDE FRACTION 3 | |
| CHITIN 50 + GLUTAMATE | |
| CHITIN 50 + GLUTAMATE | |
| CHITIN 50 CHLORIDE | |
| CHITIN 50 CHLORIDE | |
| SEACURE CHITOSAN GLUTAMATE G210 | |
| SEACURE CHITOSAN GLUTAMATE G210 | |
| SEACURE CHITOSAN GLUTAMATE G110 | |
| SEACURE CHITOSAN CHLORIDE CL 110 | |
| SEACURE CHITOSAN GLUTAMATE G210 | |
| SEACURE CHITOSAN GLUTAMATE G210 | |
| SEACURE CHITOSAN GLUTAMATE G210 | |
| INTRA NASAL FLUVIRIN | |
| SUBCUTANEOUS FLUVIRIN | |

HAI-GMT (10 to 1000, log scale)

INFLUENZA VACCINE COMPOSITION WITH CHITOSAN ADJUVANT

CROSS REFERENCE TO RELATED APPLICATION

This application is a continuation of International Application No. PCT/GB98103534, filed Nov. 27, 1998, the disclosure of which is incorporated herein by reference.

BACKGROUND OF THE INVENTION

This invention relates to a vaccine composition for intranasal administration comprising one or more influenza antigens, and a chitosan as a mucosal adjuvant. The invention also relates to methods of immunization using the vaccine compositions, and to the use of certain chitosans for enhancing the immunogenicity of influenza viral antigens, when administered intranasally.

Current influenza vaccines consist of either inactivated whole virus, disrupted virus (split vaccines) or purified preparations of the membrane glycoproteins haemagglutinin (HA) and neuraminidase (NA) sub-unit vaccines. Haemagglutinin and neuraminidase are the antigens to which protective antibody responses are directed, haemagglutinin being the major protective antigen. Estimates of the efficacy of these parenterally administered vaccines vary greatly. Such vaccines are believed to act primarily by eliciting circulating anti-haemagglutinin IgG antibodies that transudate into the lower respiratory tract.

M. L. Clements et al, J. Clinical Microbiology 24, 157–160, 1986, have previously reported that both secretory IgA and serum IgG participate in immunity to influenza virus. Moreover, in mice, a number of published studies have demonstrated the importance of respiratory IgA to protection against influenza infection. It has also been found that an advantage of stimulating a local IgA response to influenza is that it is often of a broader specificity than the serum response and thus can provide cross-protection against viruses possessing haemagglutinin molecules different from those present in the vaccine. Accordingly, influenza vaccines that elicit both local secretory and serum antihaemagglutinin responses should provide superior immunity to current vaccines. However, parenteral vaccination (intramuscular, sub-cutaneous etc.) is not effective at eliciting local antibody production, if there has been no previous mucosal exposure (e.g. infection). In order to stimulate the mucosal immune system, the vaccine must be applied topically to a mucosal surface.

Mucosal administration of influenza vaccine would have a number of advantages over traditional parenteral immunization regimes. Paramount amongst these are more effective stimulation of the local mucosal immune system of the respiratory tract and the likelihood that vaccine uptake rates would be increased because the fear and discomfort associated with injections would be avoided. Accordingly, a number of attempts have been made to develop mucosal influenza vaccines. A drawback however is that inactivated vaccines are often poorly immunogenic when given mucosally. For example, Kuno-sakai et al (vaccine 12: 1303–1310, (1994) have shown that administration of inactivated vaccine to humans gave strong mucosal and serum antibody responses and was effective in preventing infection by live vaccine virus. However, in order to achieve such results, Kuno-sakai et al administered three times the commercially available dose, an approach which is not considered to be commercially viable. In order to overcome this problem, different approaches to improving the immunogenicity of flu vaccines given orally or intranasally have included the use of the B sub-unit of cholera toxin (CTB) as an adjuvant (see S. Tamura et al, vaccine, 6, 409, (1988), encapsulation of the vaccine in a variety of microspheres (see Z. Moldoveanu et al, J. Inf. Dis. 167, 85–90 (1993), and the use of live attenuated strains (see H. F. Maassab et al vaccines, Plotkin S. A. and Mortimer F. A. Jr (eds) W. B. Saunders Philadelphia p435 (1993). To date however, the aforementioned approaches to the problem of poor mucosal immunogenicity have not resulted in the development of any commercially practicable means of enhancing the immunogenicity of mucosally administered flu vaccines, so far as the present applicants are aware.

The aforementioned problems have been solved to a very considerable extent by the compositions described in our earlier patent applications numbers WO-A-96 10421 and PCT/GB96/02680 (WO-A-97 16208) which disclose the use of chitosans as mucosal adjuvants. However, despite the efficacy of the compositions disclosed in our earlier applications, there remains room for improvement, particularly with regard to the pharmaceutical properties of the compositions, such as their long term stability.

Chitosan is a linear polysaccharide formed from repeating beta (1-4 linked) N-acetyl-D-glucosamine and D-glucosamine units, and is derived from the partial deacetylation of chitin obtained from the shells of crustaceans. Chitosan is usually made commercially by a heterogeneous alkaline hydrolysis of chitin to give a product which possesses a random distribution of remaining acetyl moieties. The properties of chitosans depend upon inter alia the degree of deacetylation, and the molecular weight. Most commercially available chitosans contain a population of chitosan molecules of varying molecular weights and varying concentrations of the component N-acetyl-D-glucosamine and D-glucosamine groups. The immunological properties of chitosans are known to be linked to the ratio between the N-acetyl-D-glucosamine and D-glucosamine groups.

The use of chitosans in an immunological context has been disclosed in articles by J. Iida et al. *Vaccine*, Vol. 5, pp 270–273 and K. Nishimura et al. *Vaccine*, 1984, Vol. 2, 99 94–100. Iida et al. and Nishimura et al. both disclosed the results of tests on chitosans having 30% and 70% deacetylation.

EP-A-0 183556 discloses the use of chitin and chitosan oligomers containing from two to seven glycosidic units as immune potentiating agents. The oligomers disclosed in this document are either fully deacetylated or contain the full complement of N-acetyl groups. There are no disclosures of partially deacetylated compounds. The highest molecular weight chitosan oligomer disclosed in this document would have a molecular weight of approximately 1439, which is a tiny fraction of the molecular weights (typically 500,000) of commercially available chitosan polymers.

WO-A-90 09780 discloses the use of various polycationic substances, such as chitosans, as mucosal absorption enhancers. This document contains a specific example illustrating the use of the "Sea Cure +" grade of chitosan (obtainable from Protan Biopolymer A/S, Drammen, Norway) as an intranasal absorption enhancer for insulin. However, there is no disclosure or suggestion in this document that chitosans may act as vaccine adjuvants. The polycationic substances disclosed in this document are essentially high molecular weight polymers and, although it is stated that the polymers can have molecular weights of as low as 10,000, it is preferred that the molecular weights are at least 100,000 or 200,000 and most preferably about 500,000.

In WO-A-97/20576, it is disclosed that chitosans can be used as mucosal adjuvants for a wide variety of antigens. It is also disclosed in WO-A-97/20576 that the chitosan can have a molecular weight between 10 kD and 500 kD, molecular weights of between 50 kD and 300 kD being preferred and molecular weights of 10 kD to 300 kD being more preferred. Although influenza compositions identical to those in our earlier application WO-A-96 10421 are exemplified, it is stated to be preferred that the antigen is not an influenza antigen, and there is no disclosure of influenza antigen compositions containing chitosans of less than 100,000 kD weight average molecular weight, nor is there any discussion as to the importance of molecular weight to solution stability.

SUMMARY OF THE INVENTION

In our earlier patent applications WO-A-96 10421 and PCT/GB96/02680 (WO-A-97 16208A), it is disclosed that by administering the haemagglutinin and neuraminidase antigens of influenza together with a particular chitosan derivative in an intranasal formulation, it is possible to achieve good IgG and good IgA responses. It has now been found that by selecting certain grades of chitosans, and in particular chitosans of defined molecular weights, it is possible to provide formulations having improved long term stability.

The efficacy of chitosans as adjuvants depends to a considerable extent on the extent of the level of deacetylation. Chitosans having only low levels of deacetylation have very poor adjuvant properties, at least insofar as influenza vaccine antigens are concerned. It has been found by the present inventors that for good adjuvant properties, the chitosan should be at least 80% deacetylated.

Chitosans having this level of deacetylation are relatively insoluble in water in the free base form and therefore are usually presented in the form of acid addition salts such as glutamate salts. Such salts can be formed by dissolving the free base form of the chitosan in acid and then drying. Because of the high proportion of free amino groups (which have a pKa of about 6.6) available for reaction with acids, acid addition salts of highly deacetylated chitosans are ad: significantly more acidic than chitosans having a lower level of deacetylation. Thus, acid addition salts of chitosans having approximately 85% deacetylation form solutions having a pH of about 4 to 5. However, a problem with preparing solutions at pH 4, particularly vaccine solutions containing influenza vaccine antigens, is that influenza antigens are susceptible to degradation and loss of activity at low pH, such as pH 4. Indeed, even at pH values as high as pH 6, it has been found by the applicants that the influenza antigens are relatively unstable on storage and that there is an appreciable loss of activity. It will be appreciated therefore that there is a conflict between the need, on the one hand, to optimise the adjuvant activity of the chitosan by using a highly deacetylated form, and the equally important need on the other hand to ensure stability of the antigen.

It is of course possible in principle to adjust the acidity of the vaccine solution to a pH nearer to neutral at which the antigens are more stable, but a further problem is that chitosan salts such as chitosan hydroglutamate tend to be only poorly soluble, if at all, at pH 7, and this creates problems with the stability of the formulation. In particular, during long term storage, there is a tendency for precipitation of the chitosan from solution to occur. Such precipitation is clearly unacceptable in a pharmaceutical context, particularly where vaccines are concerned.

BRIEF DESCRIPTION OF THE DRAWINGS

The foregoing summary, as well as the following detailed description of embodiments of the invention, will be better understood when shown in conjunction with the appended drawings. For the purpose of illustrating the invention, there is shown in the drawings embodiments which may be preferred. It should be understood, however, that the invention is not limited to the precise arrangements and instrumentalities shown.

IN THE DRAWINGS

Figure 1:
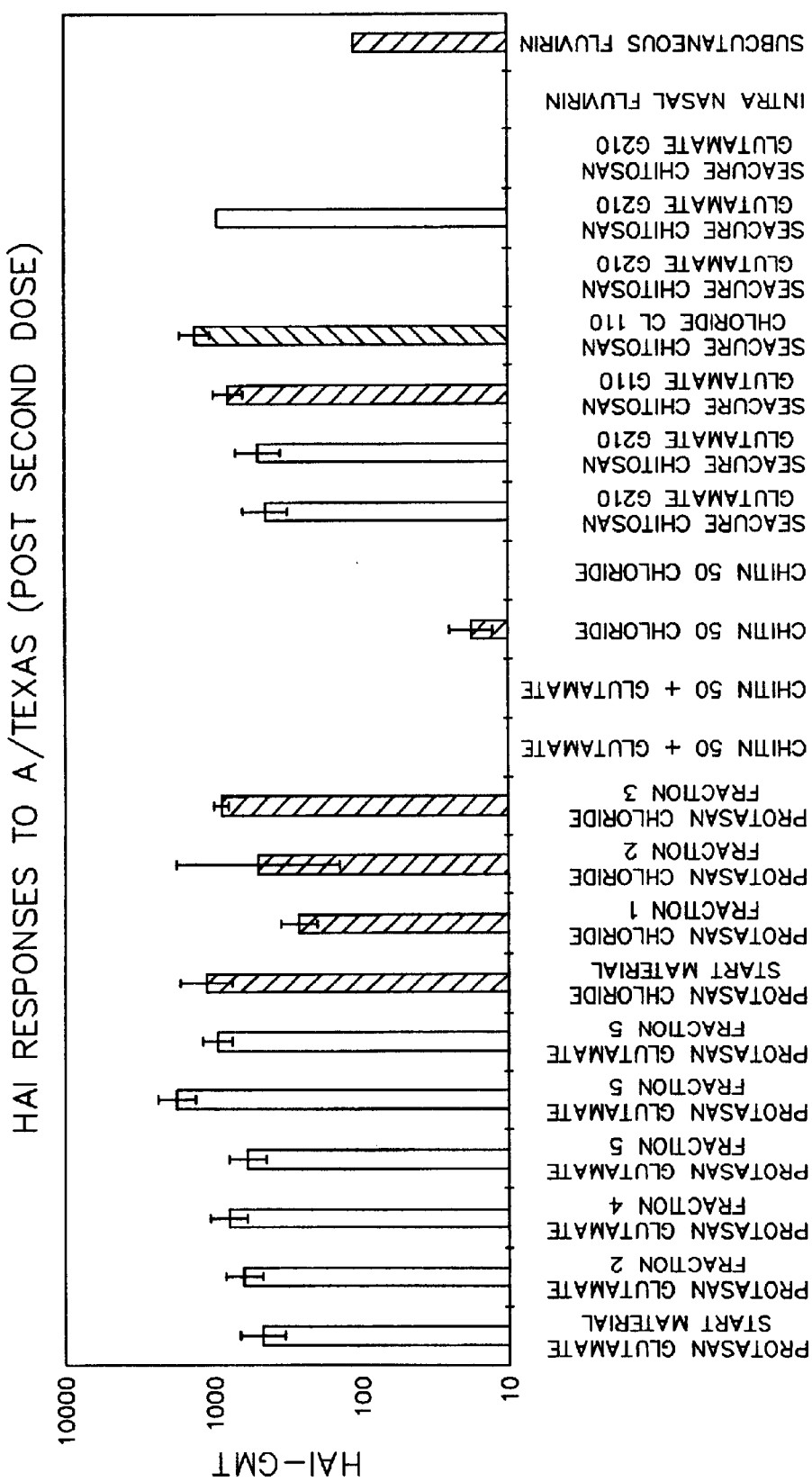

FIG. 1 shows the post-second dose serum antibody responses (HAI responses) to a purified surface influenza antigen A/Texas in female Balb/C mice vaccinated by intranasal delivery of 10 microliters of a antigenichitosan composition or a saline control solution.

Figure 2:
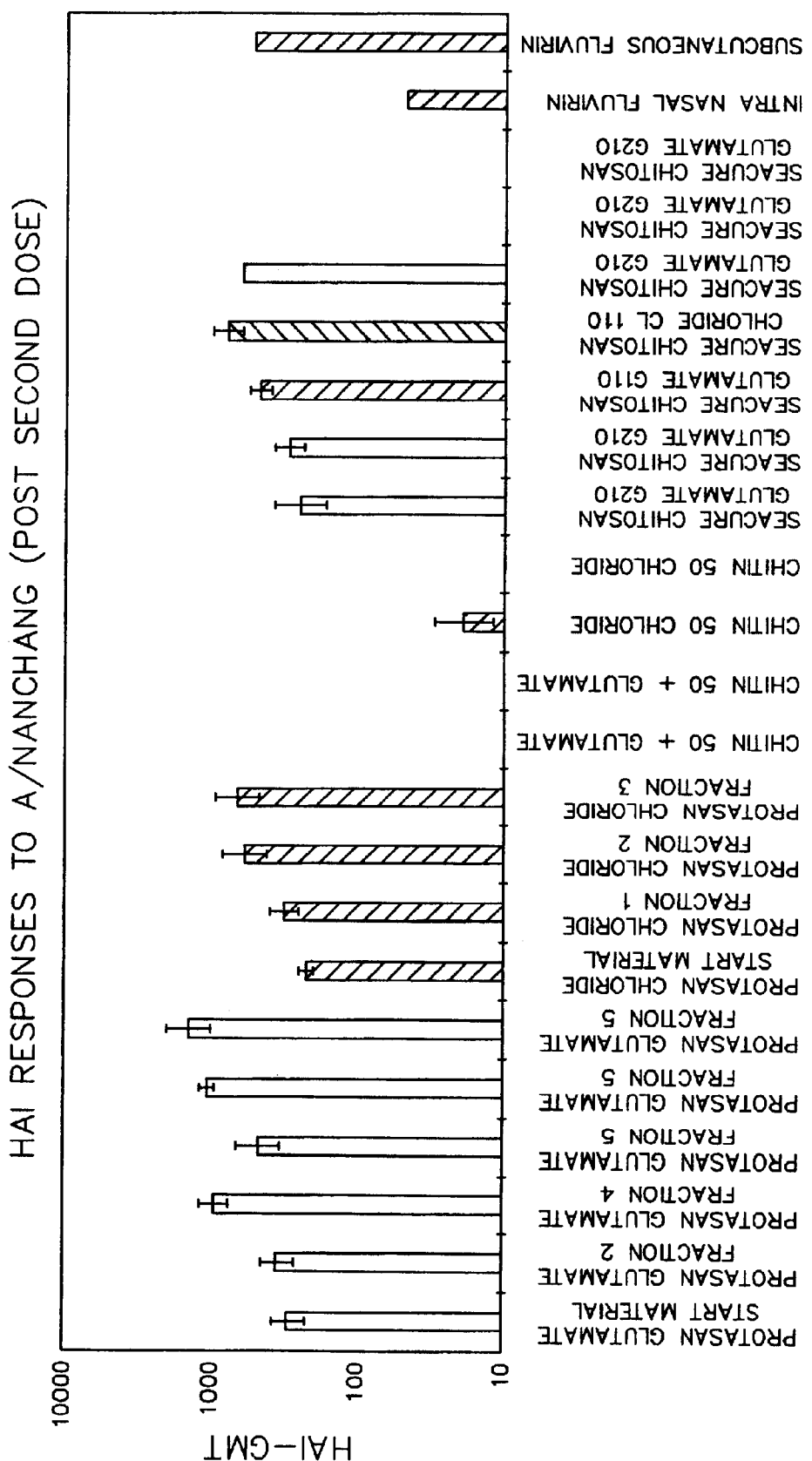

FIG. 2 shows the post-second dosed serum antibody responses (HAI responses) to a purified surface influenza antigen A/Nanchang in female Balb/C mice vaccinated by intranasal delivery of 10 microliters of a antigen/chitosan composition or a saline control solution.

FIG. 3 shows the post-second dosed serum antibody responses (HAI responses) to the purified surfsa influenza antigen B/Harbin in female Balb/C mice vaccinated by intranasal delivery of 10 microliters of a antigenichitosan composition or a saline control solution.

DETAILED DESCRIPTION OF THE INVENTION

It has now been found that by using chitosans of much lower molecular weight than have previously been used, the long term stability of chitosan formulations is greatly increased, but without affecting the adjuvancy of the chitosan. In particular, it has been found that the stability of the formulation can be improved by using chitosans which have weight average molecular weights of no greater than 100,000.

By contrast, in our earlier patent applications, the chitosan used in the examples was the Sea Cure+210 grade available from Protan Biopolymer A/S, Drammen, Norway which, although not stated in either patent application, has a weight average molecular weight of approximately 576,000.

Accordingly, in a first aspect the invention provides a vaccine composition adapted for mucosal administration; the composition comprising one or more influenza vaccine antigens and an effective adjuvant amount of an acid addition salt of a chitosan wherein the chitosan is a partially deacetylated chitin which is at least 80% deacetylated and has a weight average molecular weight of between 10,000 and 100,000.

Preferably the weight average molecular weight of the chitosan salt is in the range 11,000 to 49,000, more preferably 15,000 to 35,000, particularly 17,000 to 32,000, and most particularly 20,000 to 32,000.

The concentration of chitosan in the composition will typically be up to about 5% (w/v), for example, 0.5%, 1%, 2%, 3%, 4% or 5%.

The chitosan is one which is at least 80% deacetylated, for example 80–90%, more preferably 82–88% deacetylated, particular examples being 83%, 84%, 85%, 86% and 87% deacetylation.

The viscosity of solutions of the chitosan will vary with the molecular weight, but it preferred that the chitosan is one which has an intrinsic viscosity of less than 4 dl/g, for example from 0.2 to 4 dl/g, more typically 0.5 to 3 dl/g. Preferably the chitosan is one for which the apparent viscosity of a 1% (w/v) solution of the chitosan at 25 degrees C in 0.9% NaCl, adjusted to a pH of 6.5 with 0.1 M NaOH, as measured using a Brookfield viscometer fitted with a CP40 cone and plate set to a rotation speed of 26 rpm, is in the range 1 to 25 mPas, more preferably 1 to 15 mPas, and most preferably less than 10 mPas, for example less than 8 mPas and more particularly less than 6 mPas.

The acid addition salt is one which is formed by reaction with a suitable pharmaceutically acceptable acid. The acid may be a mineral acid or an organic acid, such as a carboxylic or dicarboxylic acid, or a dicarboxy-amino acid. Examples of acid addition salts are those formed with acids such as hydrochloric, nitric, sulphuric, acetic, phosphoric, toluenesulphonic, methanesulphonic, benzenesulphonic, lactic, malic, maleic, succinic, lactobionic, fiunaric and isethionic acids, glutamic acid and aspartic acid.

The acid chosen will be one which is compatible with the antigen and does not have a significant adverse effect on the adjuvant properties of the chitosan. Preferred acid addition salts are carboxylate salts such as glutamate salts.

The vaccine composition is preferably adapted for intranasal administration.

The influenza antigens are typically surface antigens such as haemagglutinin and neuraminidase antigens. Preferably the composition contains both haemagglutinin and neuraminidase antigens. The antigens can form part of a whole influenza vaccine composition, or they can be present as purified or substantially purified antigens.

It is preferred that the purified haemagglutinin and neuraminidase antigens are present in the form of rosettes. The rosettes preferably are particles with a radius in the range 10 to 25 nanometres.

It is preferred that the rosettes are substantially free of lipid and, moreover, it is preferred that the purified haemagglutinin and neuraminidase antigens preparation as a whole is substantially free of lipids.

An example of a haemagglutinin/neuraminidase preparation suitable for use in the compositions of the present invention is the "Fluvirin" product manufactured and sold by Evans Medical Limited of Speke, Merseyside, United Kingdom, and see also S. Renfrey and A. Watts, Vaccine, 1994, Volume 12, Number 8, pp 747–752.

The compositions can contain influenza virus antigens from a single viral strain, or from a plurality of strains. For example, the composition can contain antigens taken from up to three or more viral strains. Purely by way of example the composition can contain antigens from one or more strains of influenza A together with antigens from one or more strains of influenza B.

Examples of influenza strains are strains of influenza A/Texas/36/91, A/Nanchang/933/95 and B/Harbin/7/94).

In a further aspect, the invention provides a method of immunizing a host against infection with an infective agent, which method comprises administering to a mucosal surface of the host (preferably intranasally) a vaccine composition comprising one or more influenza vaccine antigens together with an effective adjuvant amount of a chitosan as hereinbefore defined.

In a further aspect, the invention provides a method of enhancing an IgA mucosal immune response and an IgG systemic immune response by administering (preferably intranasally) to a mucosal surface of the patient a vaccine composition comprising one or more influenza vaccine antigens and an effective adjuvant amount of a chitosan as hereinbefore defined.

In a still further aspect, the invention provides a method of enhancing the immune response of an influenza vaccine antigen by co-administering therewith a chitosan as hereinbefore defined.

The compositions of the invention, and in particular intranasal compositions, can be formulated as liquids or dry powders, for administration as aerosols or drops.

Compositions for administration as nasal drops may contain one or more excipients of the type usually included in such compositions, for example preservatives, viscosity adjusting agents, tonicity adjusting agents, buffering agents and the like.

The composition preferably has a pH of greater than 6 and up to 7, for example 6.2 to 6.8, e.g. approximately 6.5.

The present invention also contemplates the provision of means for dispensing intranasal formulations of influenza virus antigens hereinbefore defined, and a chitosan as hereinbefore defined. A dispensing device may, for example, take the form of an aerosol delivery system, and may be arranged to dispense only a single dose, or a multiplicity of doses.

The vaccine will be administered to the patient in an amount effective to stimulate a protective immune response in the patient. For example, the vaccine may be administered to humans in one or more doses, each dose containing 1–250 micrograms and more preferably 5–50 micrograms of influenza viral protein prepared from each strain. For example, in the case of an influenza vaccine, where haemagglutinin and neuraminidase preparations are prepared from three virus strains, e.g. 2×Influenza A and 1×Influenza B, a total dose of viral protein administered could be in the range 15–150 micrograms. Ultimately, however, the amount of antigen required to provide the necessary immune response may be determined by trial and error in accordance with known techniques.

The invention will now be illustrated, but not limited, by the following examples.

EXAMPLE 1

Determination Of Serum Antibody Responses To Influenza Haemaglutinin And Neuraminidase Purified Surface Antigens Formulated With Chitosans Of Different Molecular Weights Several commercially available chitosans and molecular weight fractions of the chitosans were obtained from Pronova Biopolymer A/S, of Oslo, Norway. The various chitosans were formulated with influenza purified surface antigens and the resulting vaccine compositions were tested for their immunogenic properties following intranasal administration to mice. The twenty three vaccine compositions are listed in Table 1 and the properties of the chitosans used in the compositions are set out in table 2.

The influenza antigens used in the compositions were derived from the 1996/97 season "Fluvirin" vaccine product available from Evans Medical Limited, Speke, Liverpool, United Kingdom. Fluvirin (with no added thiomersal), which consists of purified surface antigens from A/Texas/36/91, A/Nanchang/933/95 and B/Harbin/7/94), was concentrated approximately ten-fold in order to enable a dose of 9 micrograms of haemagglutinin to be delivered in a 10 microlitre volume (along with 10 microlitres of chitosan solution). In addition to the "Fluvirin" compositions, compositions were made up to include only a single antigen, corresponding to one of the antigens present in the mixture.

The chitosan compositions were made up by dissolving the required amount of the desired chitosan salt in 0.9% sodium chloride and then using 0. M sodium hydroxide to adjust the pH to the required value.

Vaccine compositions for intranasal delivery to female Balb/c mice were prepared by mixing the antigen and chitosan solutions (or saline control solutions) in the ratio 1:1 just prior to delivery. Each mouse was then vaccinated by intranasal delivery of 10 microlitres of composition to each nostril. The post second dose serum antibody responses are shown in FIGS. 1, 2 and 3.

As can be seen from FIG. 1, 2 and 3, the trivalent influenza vaccine delivered subcutaneously (s/c) with no adjuvant stimulated relatively poor serum antibody responses after two doses to A/Texas and B/Harbin, but stimulated a good serum response to A/Nanchang.

The 37% deacetylated chitosan (compositions 11 and 13), whether delivered as a chloride salt or as glutamate, or at any concentration or pH tested, did not stimulate a significantly better serum antibody response than vaccine antigen alone when given intranasally (i/n).

All groups receiving highly deacetylated chitosan, whether of high or low molecular weight or whether a chloride salt or glutamate salt, demonstrated a significantly higher serum antibody response to A/Texas and A/Nanchang influenza than the corresponding vaccine compositions without the chitosan. However, serum HAI responses to B/Harbin were weak in all groups. All groups, except group 1 (chitosan glutamate prior to fractionation) and group 8 (high molecular weight chitosan chloride), demonstrated significantly better serum antibody responses than antigen

TABLE 1

| Group | Flu | Route | Chitosan glutamate | Conc.* (w/v) | pH | Flu (μg) |
|---|---|---|---|---|---|---|
| 1 | Fluvirin | i/n | Protasan glutamate starting material | 1% | 6.5 | 9 |
| 2 | Fluvirin | i/n | Protasan glutamate fraction 2 | 1% | 6.5 | 9 |
| 3 | Fluvirin | i/n | Protasan glutamate fraction 4 | 1% | 6.5 | 9 |
| 4 | Fluvirin | i/n | Protasan glutamate fraction 5 | 1% | 6.5 | 9 |
| 5 | Fluvirin | i/n | Protasan glutamate fraction 5 | 2% | 6.5 | 9 |
| 6 | Fluvirin | i/n | Protasan glutamate fraction 5 | 3% | 6.5 | 9 |
| 7 | Fluvirin | i/n | Protasan chloride starting material | 0.69% | 6.5 | 9 |
| 8 | Fluvirin | i/n | Protasan chloride fraction 1 | 0.69% | 6.5 | 9 |
| 9 | Fluvirin | i/n | Protasan chloride fraction 2 | 0.69% | 6.5 | 9 |
| 10 | Fluvirin | i/n | Protasan chloride fraction 3 | 0.69% | 6.5 | 9 |
| 11 | Fluvirin | i/n | Chitin 50 + glutamate | 0.61% | 6.5 | 9 |
| 12 | Fluvirin | i/n | Chitin 50 + glutamate | 0.31% | 6.5 | 9 |
| 13 | Fluvirin | i/n | Chitin 50 chloride | 0.61% | 6.5 | 9 |
| 14 | Fluvirin | i/n | Chitin 50 chloride | 0.61% | 7.7 | 9 |
| 15 | Fluvirin | i/n | Seacure Chitosan glutamate G210 | 1% | 6.5 | 9 |
| 16 | Fluvirin | i/n | Seacure Chitosan glutamate G210 | 1% | 6.0 | 9 |
| 17 | Fluvirin | i/n | Seacure Chitosan glutamate G110 | 1% | 6.5 | 9 |
| 18 | Fluvirin | i/n | Seacure Chitosan chloride Cl110 | 0.69% | 6.5 | 9 |
| 19 | A/Texas PSA | i/n | Seacure Chitosan glutamate G210 | 1% | 6.5 | 3 |
| 20 | A/Nanchang PSA | i/n | Seacure Chitosan glutamate G210 | 1% | 6.5 | 3 |
| 21 | B/Harbin PSA | i/n | Seacure Chitosan glutamate G210 | 1% | 6.5 | 3 |
| 22 | Fluvirin | i/n | None | n/a | 7.7 | 9 |
| 23 | Fluvirin | s/c | None | n/a | 7.7 | 9 |

*(prior to mixing)

TABLE 2

| Group | Chitosan | Molecular Weight | Intrinsic Viscosity | Apparent Viscosity | pH (1% soln) |
|---|---|---|---|---|---|
| 1 | Protasan glutamate G210 starting material | 576,000 | 6.7 dl/g | 128 mPas | 5.0 |
| 2 | Protasan glutamate G210 fraction 2 | 244,000 | 4.5 dl/g | 40 mPas | 4.9 |
| 3 | Protasan glutamate G210 fraction 4 | 145,000 | 2.6 dl/g | 12 mPas | 4.5 |
| 4 | Protasan glutamate G210 fraction 5 | 24,000 | 0.6 dl/g | 2 mPas | 5.0 |
| 7 | Protasan chloride CL 210 starting material | 240,000 | 7.7 dl/g | 113 mPas | 4.8 |
| 8 | Protasan chloride CL 210 fraction 1 | 170,000 | 6.4 dl/g | 67 mPas | 4.8 |
| 9 | Protasan chloride CL 210 fraction 2 | 99,000 | 3.8 dl/g | 23 mPas | 4.8 |
| 10 | Protasan chloride CL 210 fraction 3 | 34,000 | 1.4 dl/g | 4 mPas | 4.8 |
| 11 | chitin 50 + glutamate* | nd | nd | nd | nd |
| 13 | chitin 50 chloride | 350,000 | 9.3 dl/g | 379 mPas | nd |
| 15 | Seacure chitosan glutamate G210 | — | — | — | — |
| 18 | Seacure chitosan chloride C110 | — | — | — | — |

*Chitin 50 supplied as chloride salt to which glutamic acid was added in this composition alone. This appears to be partly due to some non-responders in each of these groups.

There were no significant differences however between responses to A/Texas and B/Harbin vaccine antigen of any groups receiving any of the chitosan glutamate molecular weight fractions. Chitosan glutamate fraction 4 stimulated a significantly better serum response to A/Nanchang than the unfractionated chitosan glutamate and fraction 1 (high molecular weight material) but not fraction 5 (low molecular weight material). Fraction 5 did not stimulate a significantly better response to A/Nanchang than any of the other fractions.

There was no significant difference between serum antibody responses to B/Harbin influenza in mice receiving 1, 2 or 3% chitosan glutamate solution (fraction 5). The 2% solution of chitosan glutamate stimulated a significantly better serum antibody response to A/Texas influenza than the 1% solution. However, the 3% chitosan glutamate solution did not stimulate significantly better serum responses than either the 2% or 1% solutions. The 2% and 3% solutions stimulated significantly better serum antibody responses to A/Nanchang than the 1% solution.

Serum antibody responses to vaccine containing chitosan chloride molecular weight fractions appeared to be strain dependent. The molecular weight had no effect on the responses to B/Harbin influenza; i.e. there was no significant difference between responses to vaccine containing any molecular weight fraction. Responses to the two A strains were anomalous. For instance, responses in the group receiving chitosan chloride starting material (unfractionated) were significantly poorer than the response to the molecular weight fractions 2 and 3. In contrast, chitosan chloride starting material stimulated the most powerful serum response to A/Texas.

No mice receiving influenza vaccine intranasally with the 37% deacetylated chitosan, in either salt form, or at either pH or concentration tested, demonstrated a serum HAI response to B/Harbin. Responses in these groups were also very poor to A/Texas and A/Nanchang. The only responses to these strains were in two mice receiving chitin 50 chloride pH 6.5, and these responses were weak, and did not indicate a significant group response to the vaccine.

The Seacure chitosan salts (compositions 15) stimulated serum HAI responses when delivered intranasally whether delivered as high or low molecular weight forms or as chloride or glutamate forms.

The results of the tests show that the adjuvant effect of chitosan on the response to intranasally administered purified surface antigens was independent of the molecular weight of the chitosan (within the limits tested). Similarly, the type of chitosan salt (glutamate or chloride) had no significant effect on the adjuvant effect. However, the results did demonstrate that the adjuvant effect is dependent on the charge density on the chitosan molecule, the highly deacetylated chitosans being more effective than the less deacetylated forms.

EXAMPLE 2

One Month Stability Studies On Chitosans of Varying Weight Average Molecular Weight Solutions of the chitosans listed in Table 2 were made up at the pH and concentrations listed in Table 3 and were subjected to stability tests over a period of one month. The parameter chosen to assess the stability of the solutions was the apparent viscosity as measured at 25 degrees C using a Brookfield viscometer fitted with a CP40 cone and plate rotated at a speed of 26 rpm. In testing the appearance of the composition, an examination was made for precipitation out of solution over the test period. The apparent viscosity was tested as an indicator of stability since viscosity decreases over time as the chains of N-acetyl glucosamine and D-glucosamine break down and precipitate out of solution. The test results set out in Table 3 can be considered to provide only an approximate guide to solution stability since the solutions were not sterile-filtered before storage and hence in each solution it is most likely that a degree of microbial degradation of the chitosans was occurring. Nevertheless, the results did indicate that the higher molecular weight chitosans exhibit considerable solution instability even over a period as short as a month. For example, a 1% solution of the Protasan glutamate starting material (weight average molecular weight 576,000) initially had an apparent viscosity of 22.4 cP but this had fallen to 8.4 cP after only a month, i.e. a 62% reduction in viscosity. By comparison, a solution of the Protasan glutamate fraction 5 showed only a 25% reduction in viscosity, and this was probably due to microbial spoilage.

TABLE 3

ONE MONTH STABILITY STUDY OF CHITOSAN SALTS OF DIFFERING MOLECULAR WEIGHT RANGES

| Chitosan | Conc | pH | Day 0 | Day 5 4° C. | Day 5 25° C. | 1 Month 4° C. | 1 Month 25° C. |
|---|---|---|---|---|---|---|---|
| Protasan Glutamate start material | 1% | 6.5 | cP 22.4 pH 6.5 | cP 24.7 pH 6.72 | cP 13.8 pH 6.53 | cP 17.2 pH 6.53 | cP 8.44 pH 6.60 |
| Protasan Gutamate fraction 2 | 1% | 6.5 | cP 12.9 pH 6.5 | cP 13.1 pH 6.70 | cP 9.32 pH 6.48 | cP 8.79 pH 6.48 | cP 3.45 pH 6.51 |
| Protasan Glutamate fraction 4 | 1% | 6.5 | cP 5.35 pH 6.44 | cP 5.27 pH 6.66 | cP 4.90 pH 6.45 | cP 4.81 pH 6.50 | cP 3.53 pH 6.60 |
| Protasan Glutamate fraction 5 | 1% | 6.5 | cP 1.94 pH 6.45 | cP 1.90 pH 6.65 | cP 1.72 pH 6.50 | cP 1.63 pH 6.63 | cP 1.45 pH 6.51 |
| Protasan chloride start material | 0.69% | 6.5 | Material not stable at pH 6.5, precipitated out of solution during formulation | | | | |
| Protasan chloride fraction 1 | 0.69% | 6.5 | Material not stable at pH 6.5, precipitated out of solution during formulation | | | | |
| Protasan chloride fraction 2 | 0.69% | 6.5 | Material not stable at pH 6.5, precipitated out of solution during formulation | | | | |

TABLE 3-continued

ONE MONTH STABILITY STUDY OF CHITOSAN SALTS OF DIFFERING MOLECULAR WEIGHT RANGES

| Chitosan | Conc | pH | Day 0 | Day 5 4° C. | Day 5 25° C. | 1 Month 4° C. | 1 Month 25° C. |
|---|---|---|---|---|---|---|---|
| Protasan chloride fraction 3 | 0.69% | 6.5 | cP 2.97 pH 6.5 | Material precipitated out of solution | | | |
| Chitin 50 + glutamate | 0.61% | 6.5 | cP 27.0 pH 6.51 | cP 27.0 pH 6.72 | cP 19.4 pH 6.71 | cP 7.14 pH 6.65 | cP 2.54 pH 6.88 |
| Chitin 50 + glutamate | 0.31% | 6.5 | cP 7.12 pH 6.54 | cP 6.98 pH 6.91 | cP 6.11 pH 6.96 | cP 2.88 pH 6.74 | cP 1.70 pH 6.97 |
| Chitin 50 chloride | 0.61% | 6.5 | cP 24.6 pH 6.55 | cP 27.5 pH 6.78 | cP 20.8 pH 6.82 | cP 15.7 pH 6.62 | cP 1.11 pH 6.40 |
| Chitin 50 chloride | 0.61% | 7.7 | cP 56.2 pH 7.72 | cP 50.7 pH 7.74 | cP 25.8 pH 7.48 | cP 27.5 pH 7.46 | cP 1.07 pH 6.66 |
| Seacure chitosan glutamate G210 | 1% | 6.5 | cP 12.0 pH 6.50 | cP 8.00 pH 6.53 | cP 1.96 pH 6.67 | cP 1.51 pH 6.68 | cP 1.39 pH 7.25 |
| Seacure chitosan glutamate G210 | 1% | 6.0 | Cp 12.3 Ph 6.00 | Cp 9.52 Ph 6.12 | Cp 1.45 Ph 6.40 | Cp 1.31 Ph 6.67 | Cp 1.15 Ph 7.49 |
| Protasan chitosan glutamate G110 | 1% | 6.5 | cP 4.56 pH 6.51 | cP 4.34 pH 6.50 | cP 3.96 pH 6.53 | cP 3.22 pH 6.52 | cP 13.4 pH 7.49 |
| Protasan chitosan chloride Cl 110 | 0.69% | 6.5 | cP 4.07 pH 6.50 | cP 3.51 pH 6.34 | cP 3.11 pH 6.33 | cP 3.36 pH 6.41 | cP 3.53 pH 6.42 |

NOTE: None of the above formulations were sterile filtered (0.2 μm)

EXAMPLE 3

Stability Studies on Compositions Containing Chitosans of Differing Molecular Weights Two of the chitosan glutamate compositions exhibiting the better solution stability in the tests described in Example 2 above were subjected to further stability tests over a longer period. The two compositions were prepared from the two grades of chitosan glutamate identified as "Fraction 4" and "Fraction 5" below and corresponding to the chitosans used in Groups 3 and 4 of Table 2. Both grades of chitosan are available from Pronova Biopolymer A/S, Oslo, Norway.

| Fraction 4 | |
|---|---|
| Weight average molecular weight | 145,000 |
| Intrinsic Viscosity | 2.6 dl/g |
| Apparent viscosity (1% soln.) | 12 mPas |
| pH (1% soln.) | 4.5 |
| Deacetylation | 86% |
| Fraction 5 | |
| Weight average molecular weight | 24,000 |
| Intrinsic Viscosity | 0.6 dl/g |
| Apparent viscosity (1% soln.) | 2 mPas |
| pH (1% soln.) | 5 |
| Deacetylation | 86% |

Aqueous 1% solutions were made up and the pH of each solution adjusted to 6.5 with sodium hydroxide. The solutions were sterile-filtered through a 0.22 micron filter and filled into sterilized 3 ml tubular drawn glass vials which were then sealed with bromobutyl rubber stoppers. The solutions were stored at constant temperature (either 5 degrees C (±3 degrees) or 25 degrees C (±3 degrees) in the dark for three months and tested for appearance, pH and apparent viscosity at 0, 1 week, 1 month, two months and three months, and bioburden and endotoxin content at time 0 and three months. The results of the tests are shown in Table 4 below from which it can be seen that after three months there was no appreciable change in viscosity or pH in the lower molecular weight fraction, fraction 5 whereas there was some degradation with fraction 4.

TABLE 4

Results of Stability Tests on Fractions 4 and 5

Appearance

| Fraction | Conditions | Initial | 1 Week | 1 Month | 2 Months | 3 Months |
|---|---|---|---|---|---|---|
| 4 | 5° C. ± 3° C. | SAT | SAT | SAT | SAT | SAT |
|   | 25° C. ± 3° C. | SAT | SAT | SAT | SAT | SAT |
| 5 | 5° C. ± 3° C. | SAT | SAT | SAT | SAT | SAT |
|   | 25° C. ± 3° C. | SAT | SAT | SAT | SAT | SAT |

End-of-life specification:
Fraction 4: Transparent, pale yellow solution
Fraction 5: Clear, colourless solution
SAT = Satisfactory pH

| Fraction | Conditions | Initial | 1 Week | 1 Month | 2 Months | 3 Months |
|---|---|---|---|---|---|---|
| Fraction 4 | 5° C. ± 3° C. | 6.45 | 6.52 | 6.55 | 6.49 | 6.46 |
|  | 25° C. ± 3° C. | N/A | 6.46 | 6.51 | 6.49 | 6.46 |
| Fraction 5 | 5° C. ± 3° C. | 6.49 | 6.52 | 6.53 | 6.52 | 6.48 |
|  | 25° C. ± 3° C. | N/A | 6.47 | 6.54 | 6.55 | 6.47 |

End-of-life specification: Fraction 4 and 5: 6.3–7.0

Apparent Viscosity (cP)

| Fraction | Conditions | Initial | 1 Week | 1 Month | 2 Months | 3 Months |
|---|---|---|---|---|---|---|
| Fraction 4 | 5° C. ± 3° C. | 5.87 | 5.72 | 5.72 | 5.20 | 5.18 |
|  | 25° C. ± 3° C. | N/A | 5.89 | 5.54 | 5.15 | 4.99 |
| Fraction | 5° C. ± 3° C. | 1.76 | 2.71 | 1.87 | 1.90 | 2.03 |

TABLE 4-continued

Results of Stability Tests on Fractions 4 and 5

| | 25° C. ± 3° C. | N/A | 2.59 | 1.89 | 1.88 | 2.34 |
|---|---|---|---|---|---|---|

End-of-life specification
Fraction 4 and 5: CP40 (26 rpm) 1.5–6.0 cp at 25° C.

| | Bioburden |
|---|---|
| Fraction | Initial |
| Fraction 4 | Day 0 < cfu/20 ml |
| Fraction 5 | Day 0 < 1 cfu/20 ml |
| End-of-life specification: | |
| Fraction 4 and 5: ≦ 100 cfu/ml | |

From the results set out in the examples, it can be seen that whereas the adjuvant activity of the chitosan is largely independent of either the type of salt used or the molecular weight of the chitosan, the stability of the formulation does depend considerably on the molecular weight, with the lower molecular weight fractions providing much better long term stability and ease of formulation. In addition, a further advantage of the lower molecular weight fractions is the fact that they can be filtered through a 0.22 micron filter (generally considered to be a means of sterilizing a solution) whereas the molecular weight fractions of 100,000 and over cannot generally pass through such a filter.

It will be appreciated that the foregoing examples are merely intended to be illustrative of the invention and not limitative of the scope of the invention which is defined in the claims appended hereto.

We claim:

1. A vaccine composition adapted for mucosal administration, the composition comprising one or more influenza vaccine antigens and an effective adjuvant amount of an acid addition salt of a chitosan, wherein the chitosan is a deacetylated chitin, the chitin being at least 80% deacetylated, and the chitosan has an apparent viscosity of less than 10 mPas in a 1% w/v solution at 25° C. in 0.9% NaCl, adjusted to pH 6.5 with 0.1 M NaOH as measured using a Brookfield cone and plate viscometer.

2. A vaccine composition according to claim 1 wherein the chitosan salt is the salt of a carboxylic or dicarboxylic acid, or a dicarboxy-amino acid.

3. A vaccine composition according to claim 2 wherein the chitosan salt is selected from salts of lactic, malic, maleic, succinic, lactobionic, fumaric, glutamic and aspartic acid salts.

4. A vaccine composition according to claim 1 which contains both haemagglutinin and neuraminidase influenza virus antigens.

5. A vaccine composition according to claim 1 which is adapted for intranasal administration.

6. A vaccine composition according to claim 1 wherein the chitosan is 80–90% deacetylated.

7. A vaccine composition according to claim 6 wherein the chitosan is 82–88% deacetylated.

8. A vaccine composition according to claim 7 wherein the chitosan is 83%, 84%, 85%, 86% or 87% deacetylated.

9. A vaccine composition according to claim 1 wherein the composition has a pH of greater than 6 and up to 7.

10. A vaccine composition according to claim 9 wherein the pH is in the range of 6.2 to 6.8.

11. A vaccine composition according to claim 1 wherein the apparent viscosity of the chitosan is less than 8 mPas.

12. A vaccine composition according to claim 11 wherein the apparent viscosity of the chitosan is less than 6 mPas.

13. A vaccine composition according to claim 1 wherein the concentration of chitosan in the composition is up to about 5% (w/v).

14. A pharmaceutical product comprising a dispensing device adapted to deliver a composition intranasally, in combination with a vaccine composition, wherein said vaccine composition is as defined in claim 1.

15. A pharmaceutical product according to claim 14 wherein the dispensing device is an aerosol delivery system.

16. A vaccine composition according to claim 10 wherein the pH is approximately 6.5.

17. A method of immunizing a host against infection with influenza comprising administering the vaccine composition of claim 1 to a mucosal surface of the host.

18. A method of enhancing an IgA mucosal immune response and an IgG systemic immune response comprising administering the vaccine composition of claim 1 to a mucosal surface of a patient.

19. A method of enhancing the immune response of an intranasally administered vaccine antigen comprising co-administering therewith the vaccine composition of claim 1.

* * * * *